United States Patent [19]

Crayton et al.

[11] Patent Number: 5,608,315

[45] Date of Patent: Mar. 4, 1997

[54] APPARATUS FOR DETECTING PARTICLES IN A FLUID AND A METHOD FOR OPERATING SAME

[75] Inventors: John W. Crayton, Washington; John J. Krone, Dunlap; Terry D. Oltman, Chillicothe, all of Ill.

[73] Assignee: Caterpillar Inc., Peoria, Ill.

[21] Appl. No.: 517,228

[22] Filed: Aug. 21, 1995

[51] Int. Cl.$^6$ .......................... G01N 27/74; G01R 33/12
[52] U.S. Cl. .................. 324/204; 324/225; 324/232; 324/236; 340/631
[58] Field of Search ...................... 324/204, 225, 324/232, 234, 236; 340/631; 73/61.42; 210/85

[56] References Cited

U.S. PATENT DOCUMENTS

| | | | |
|---|---|---|---|
| 2,671,200 | 3/1954 | Lederer | 324/71 |
| 3,748,576 | 7/1973 | Sigournay | 324/41 |
| 3,878,103 | 3/1975 | Miller et al. | 210/243 |
| 4,004,216 | 1/1977 | Natens et al. | 324/41 |
| 4,176,545 | 12/1979 | Oddo | 73/64 |
| 4,219,805 | 8/1980 | Magee et al. | 340/631 |
| 4,523,146 | 6/1985 | Champaigne | 324/204 |
| 4,536,713 | 8/1985 | Davis et al. | 324/324 |
| 4,553,094 | 11/1985 | Gehrke | 324/225 |
| 4,563,644 | 1/1986 | Lenander et al. | 324/232 |
| 4,651,091 | 3/1987 | Chambers et al. | 324/204 |
| 4,651,092 | 3/1987 | Brunsch et al. | 324/204 |
| 4,731,578 | 3/1988 | Tsaprazis | 324/204 |
| 4,766,373 | 8/1988 | Chambers et al. | 324/204 |
| 4,831,362 | 5/1989 | Tsaprazis | 340/515 |
| 4,837,511 | 6/1989 | Whittington et al. | 324/236 |
| 4,841,244 | 6/1989 | Chambers | 324/204 |
| 4,860,756 | 8/1989 | Ko et al. | 324/232 X |
| 4,878,019 | 10/1989 | Tsaprazis et al. | 324/204 |
| 4,893,079 | 1/1990 | Kustra et al. | 324/225 |
| 4,926,120 | 5/1990 | Veronesi et al. | 324/204 |
| 5,001,424 | 3/1991 | Kellett et al. | 324/204 |
| 5,027,065 | 6/1991 | Bares et al. | 324/204 |
| 5,061,364 | 10/1991 | Metala et al. | 210/85 |
| 5,118,410 | 6/1992 | Rumberger | 210/85 |
| 5,334,932 | 8/1994 | Nielsen | 324/204 |
| 5,388,448 | 2/1995 | Showalter et al. | 73/61.71 |
| 5,444,367 | 8/1995 | Kempster et al. | 324/204 |

FOREIGN PATENT DOCUMENTS

| | | | |
|---|---|---|---|
| 2101330 | 1/1983 | United Kingdom | 324/204 |
| 2132358 | 7/1984 | United Kingdom . | |

*Primary Examiner*—Gerard R. Strecker
*Attorney, Agent, or Firm*—David M. Masterson; Mario J. Donato

[57] ABSTRACT

In one aspect of the present invention, an apparatus for detecting particles within a fluid is disclosed. A bobbin defines a debris collection chamber. Spaced apart first and second coils are wound about the bobbin in the proximity of the debris collection chamber, wherein the inductance of the coils are responsive to the particle accumulation within the collection chamber. An electromagnet is wound about the second coil to attract ferrous particles into the proximity of the second coil. A reference coil is wound about the bobbin to compensate for the changing temperature of the fluid. An oscillator is coupled to the first, second and reference coils for selectively producing an oscillating waveform at a frequency that induces eddy currents in the particles. The frequency of the oscillating waveform is indicative of the amount of accumulation of both the ferrous and non-ferrous particles.

19 Claims, 4 Drawing Sheets

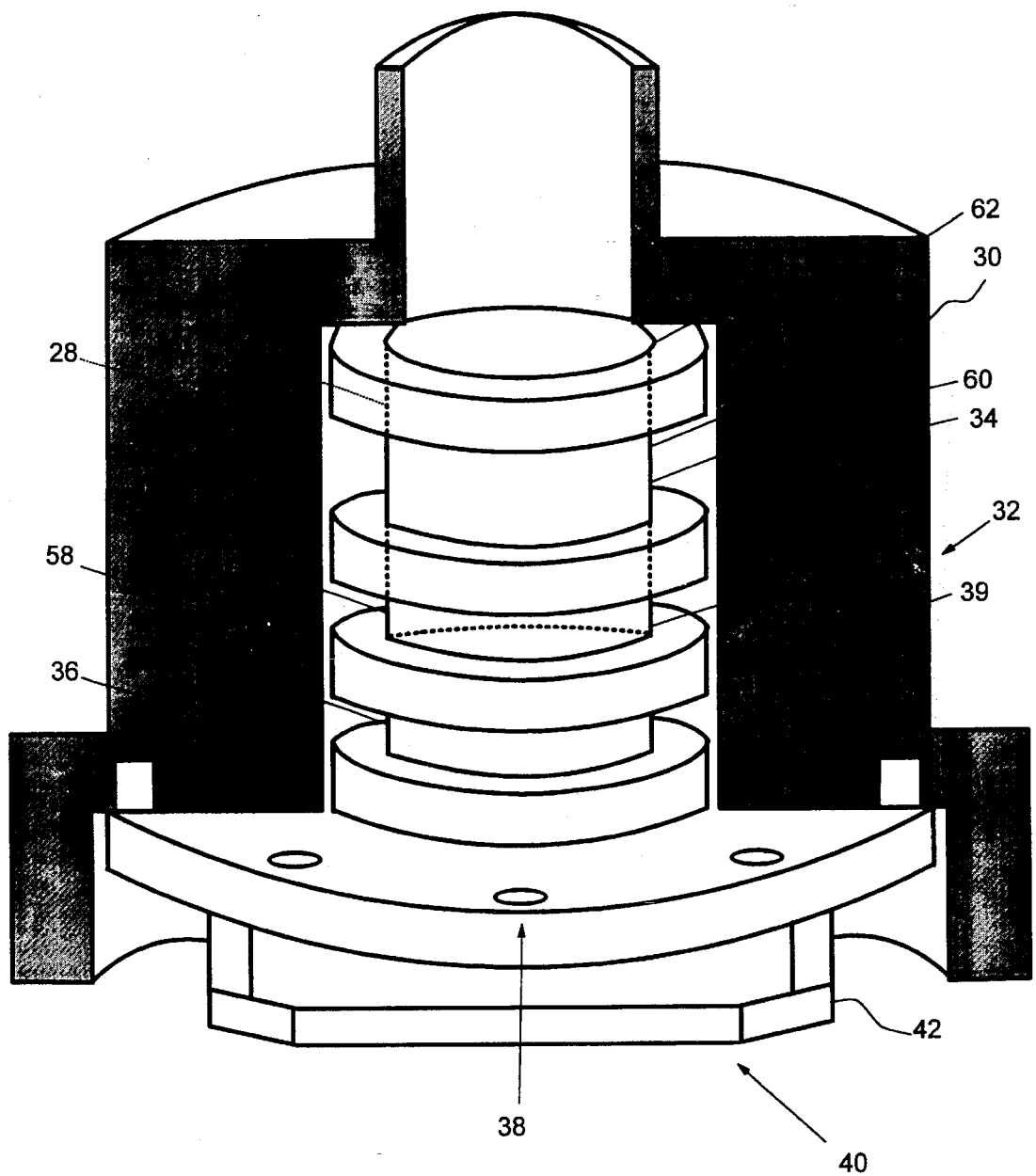
Fig_2_

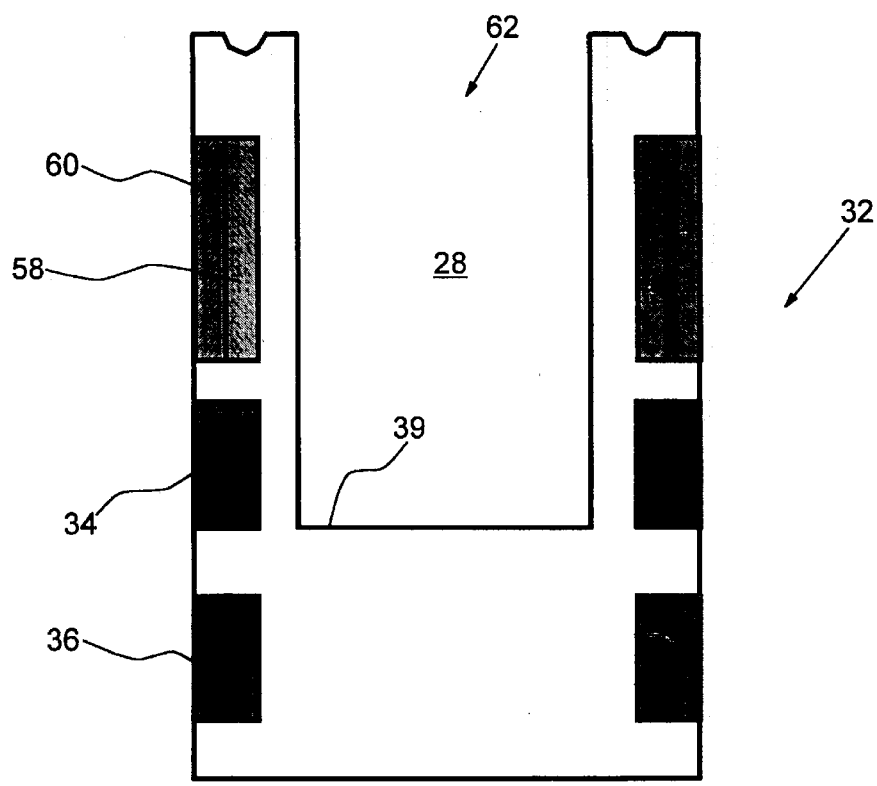
Fig_3_
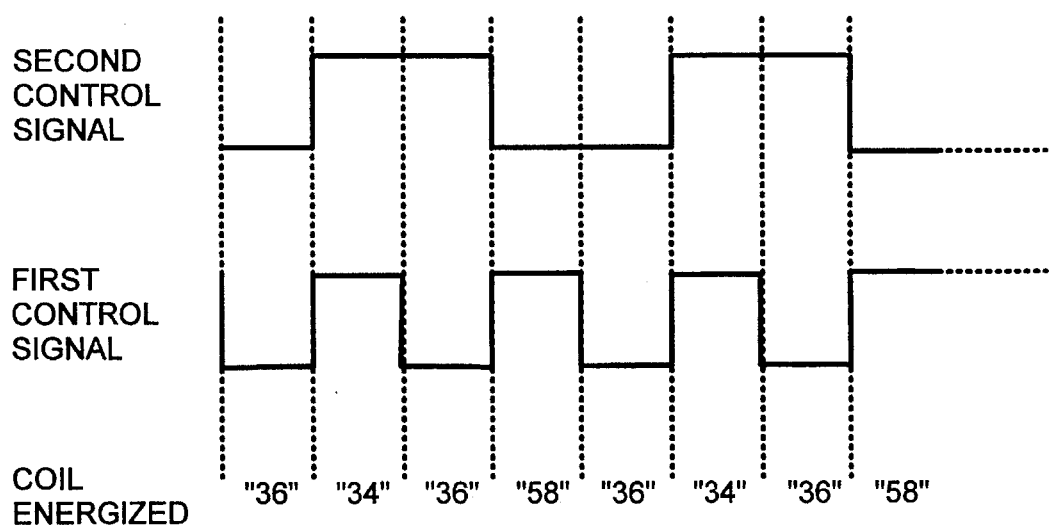
Fig_5_

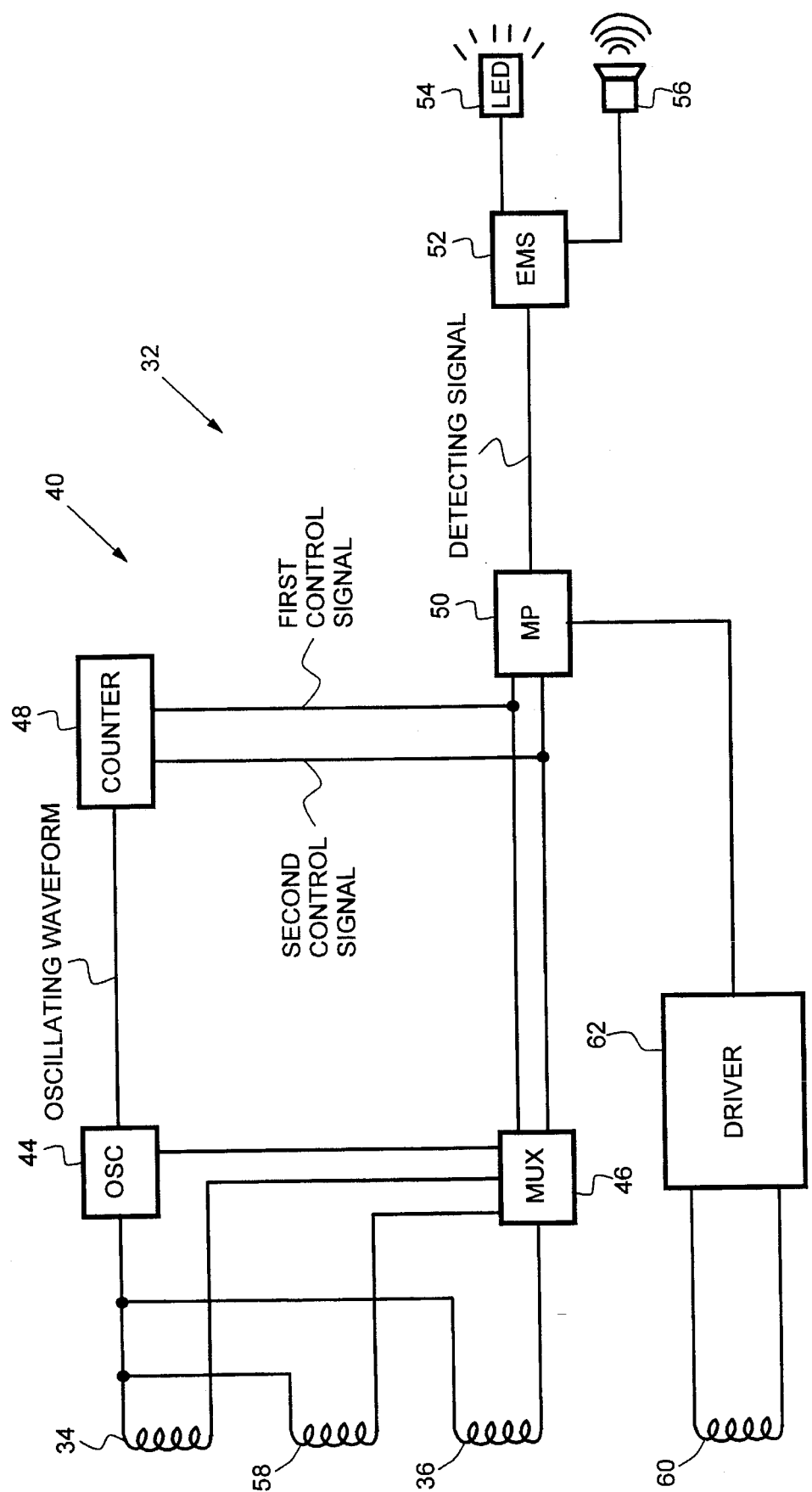
Fig-4-

APPARATUS FOR DETECTING PARTICLES IN A FLUID AND A METHOD FOR OPERATING SAME

TECHNICAL FIELD

This invention relates generally to an element in a fluid system, and more particularly, to a device for detecting ferrous and non-ferrous metallic particles in a fluid.

BACKGROUND ART

Hydraulic systems are important to many work machines and represent large expenses in the event of component failure. If failures are detected early, repair expenses can be minimized; however, if catastrophic failure occurs, the large amounts of particles caused by the failure can enter the hydraulic system and cause damage to many other components. Fortunately, any catastrophic failure of one of the components is often preceded by the gradual breakup of one or more components. This break-up can be detected so that corrective action can be taken before any further damage to surrounding components occurs.

In the past, there have been several different ways to detect metallic particles within a fluid. One such system is described by Magee et al. in U.S. Pat. No. 4,219,805. This system captures ferrous particles that are contained in a fluid medium, and indicates the mass of any significant individual ferrous particles and the total mass of such particles that have accumulated over a predetermined time period. However, this system is limited to the detection of ferrous particles, e.g., iron; as opposed to non-ferrous particles, e.g., copper, brass, or non-magnetic stainless steel.

The present invention is directed to overcoming one or more of the problems set forth above.

DISCLOSURE OF THE INVENTION

In one aspect of the present invention, an apparatus for detecting particles within a fluid is disclosed. A bobbin defines a debris collection chamber. Spaced apart first and second coils are wound about the bobbin in the proximity of the debris collection chamber, wherein the inductance of the coils are responsive to the particle accumulation within the collection chamber. An electromagnet is wound about the second coil to attract ferrous particles into the proximity of the second coil. A reference coil is wound about the bobbin to compensate for the changing temperature of the fluid. An oscillator is coupled to the first, second and reference coils for selectively producing an oscillating waveform at a frequency that induces eddy currents in the particles. The frequency of the oscillating waveform is indicative of the amount of accumulation of both the ferrous and non-ferrous particles.

BRIEF DESCRIPTION OF THE DRAWINGS

For a better understanding of the present invention, reference may be made to the accompanying drawings in which:

FIG. 2 is a partial, cutaway view of a debris sensing apparatus that includes three self-induction coils and an electromagnet;

FIG. 3 is a cross-sectional view of the debris sensing apparatus; and

FIG. 4 is a block diagram of the electronic circuitry associated with the three-coil particle sensing apparatus; and FIG. 5 is a timing diagram of the control signals associated with the electronic circuitry.

BEST MODE FOR CARRYING OUT THE INVENTION

Figure 1:
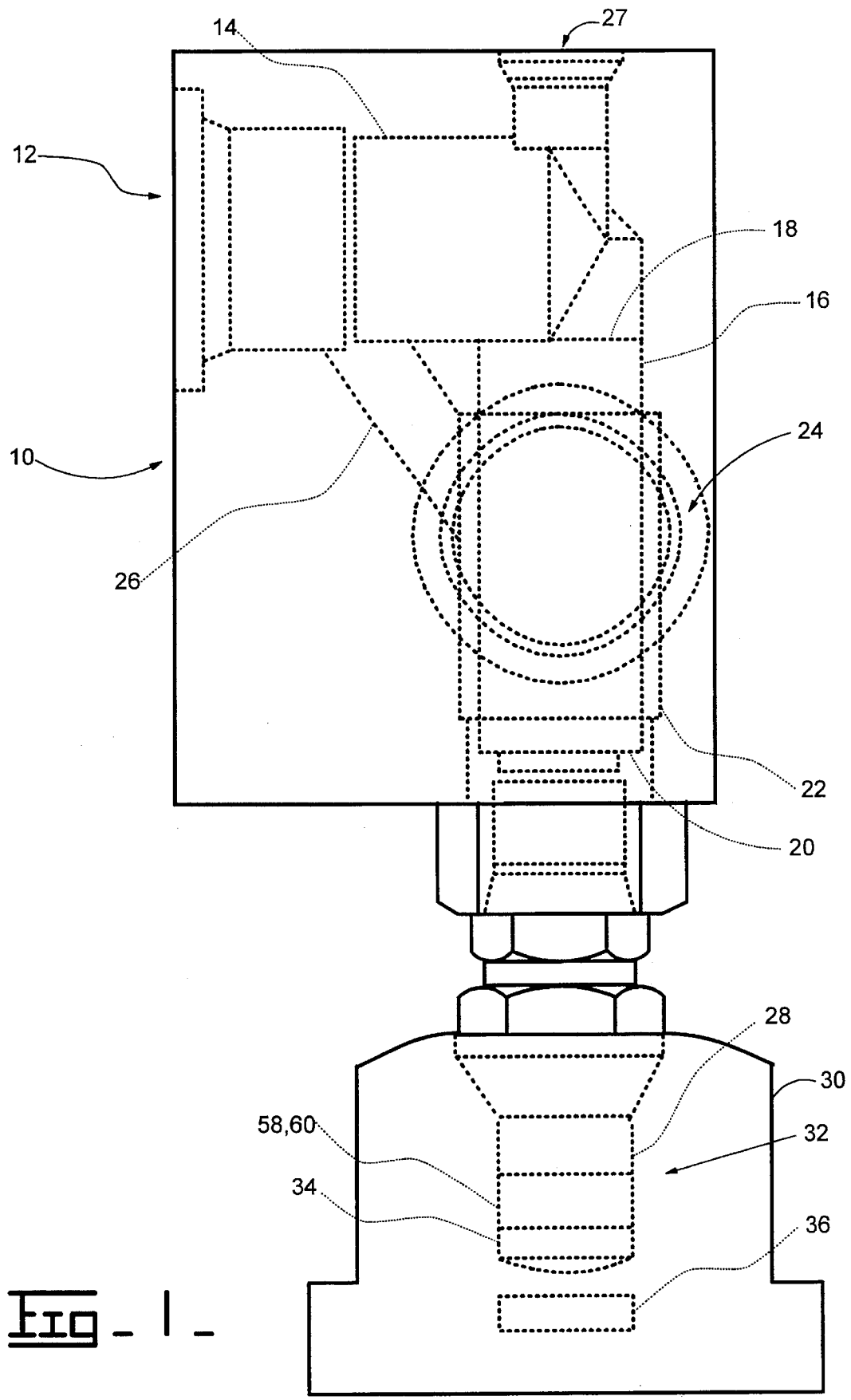
FIG. 1 is a diagrammatic view of a housing that includes an apparatus for filtering debris in a fluid and an apparatus for sensing such debris.

Referring to FIG. 1, an apparatus for filtering debris from a fluid and indicating the accumulation of the debris is referred to generally by the reference 10. An inlet port 12 is adapted for connection to a hydraulic fluid line and directs fluid to an inlet chamber 14. The inlet chamber 14 is cylindrical in shape and is preferably disposed at substantially a right angle to a screen 16. It should be understood, however, that the precise angular relationship of the inlet chamber 14 and screen 16 is not critical.

In the preferred embodiment, the screen 16 is cylindrical in shape and of approximately the same diameter as the inlet chamber 14. Advantageously, the screen 16 is formed of stainless steel "40" mesh and is open on each end 18, 20 of the cylinder formed by the screen 16. While this particular screen is not required, the screen is advantageously made of non-magnetic material and has a mesh size small enough to catch most particles while not significantly restricting flow. Fluid flows freely from the inlet chamber 14 downwardly into the cylinder defined by the screen 16 through the top opening 18. The screen 16 preferably extends coaxially in a screen chamber 22 of slightly larger diameter than the screen 16.

As is appreciated by those skilled in the art, the amount that the screen chamber 22 is larger than the screen 16 must be sufficient to not restrict the flow of fluid. The screen chamber 22 is connected to an outlet port 24 that allows fluid flowing out of the screen 16 into the screen chamber 22 to exit the apparatus 10. Thus, the fluid entering the top of the cylinder defined by the screen 16 is filtered as it passes radially outwardly through the screen 16 into the screen chamber 22. The filtered fluid then exits the apparatus 10 via the outlet port 24.

A bypass port 26 extends between the inlet port and chamber 12, 14 and the screen chamber 22. As shown, the bypass port 26 preferably extends downwardly and radially inwardly toward the screen 16. By virtue of this arrangement, fluid flows in a direction counter to a flow of fluid out of the screen. This serves to dislodge some of the debris that has become lodged in the screen 16 and urge it downwardly toward the bottom opening 20. The bypass port 26 also provides an additional flow path when the fluid becomes more viscous from low temperatures. As viscosity increases the amount of back pressure on the inlet line also increases because of the added difficulty of oil flowing through the screen 16. The bypass port 26 thus serves to alleviate some of the back pressure which can cause catastrophic failure of pumps having an external case drain.

A screen inspection and sensor port 27 is provided to allow visual inspection of the screen and to allow probes and sensors to be connected to the apparatus 10 for diagnostic purposes. For example, temperature or pressure sensors may be connected into this port for hydraulic system diagnosis. Similarly, oil samples may be taken through the screen inspection and sensor port 27. The screen 16 may also be visually inspected via this port to determine the extent of screen plugging.

The bottom opening 20 of the cylinder defined by the screen 16 is located above an opening extending into a debris collection chamber 28. Thus debris trapped by the screen 16 is pulled downwardly toward the debris collection chamber 28 by gravity and by the flow created by the bypass port 26. The debris collection chamber 28 is formed in a sensor housing 30. Preferably, the sensor housing 30 is cylindrical in shape. In the preferred embodiment, a debris sensor 32 is located adjacent the debris collection chamber 28 to detect the presence of the debris, i.e., both ferrous and non-ferrous metallic particles.

Reference is now made to FIG. 2, which shows a cross-sectional view of the sensor housing 30. In this view, the debris sensor 32 includes three self-induction coils 34, 36, 58 that are wound in the form of a helix about the plastic bobbin 38. The first coil 34 is wound on the bobbin 38 about the collection chamber 28 and adjacent to the bottom 39 of the collection chamber 28, while the reference coil 36 is wound on the bobbin 38 underneath the collection chamber 28. A second coil 58 is wound on the bobbin 38 between the first coil 34 and reference coil 36. An electromagnet 60 is wound on the bobbin 38 about the collection chamber 28 adjacent to the opening 62 of the collection chamber 28. This arrangement is additionally shown in FIG. 3, which is a cross-sectional view of the debris sensor 32.

The induction of the first coil 34 is responsive to the particle accumulation of both the ferrous and non-ferrous particles in the collection chamber 28. However, because the electromagnet 60 is used to attract ferrous particles into the proximity of the second coil 58, the second coil 58 is said to be responsive to the accumulation of ferrous particles only. The reference coil 36 is used to compensate for any temperature effects of the fluid. Thus, the inductance of the reference coil 36 is used as a baseline for determining the presence of particles within the cavity. In the preferred embodiment, the first and second coils 34, 58, as well as, the reference coil 36 are identical and are constructed of # 30 insulated wire with 200 turns. The electromagnet 60 is constructed of # 30 insulated wire with 1000 turns.

The electronic circuitry 40 that is associated with the three-coil sensor is disposed on a circuit board 42 that is located at the bottom of the housing 30 and is described with reference to FIG. 4. Note, the circuit shown in FIG. 4 is exemplary, and the manner of design and construction of this, or a similar circuit, would be commonly known to a person skilled in the art. An oscillator 44 produces an oscillating waveform. The frequency of the oscillating waveform is dependant upon a parallel resonant circuit comprising one of the self-inductive coils 34, 36, 58 and a capacitor (not shown). Preferably, the oscillator 44 produces the oscillating waveform at a high frequency, e.g., approximately 300 kHz. However, as the self-inductance of the coils 34, 36, 58 change, so does the frequency of the oscillating waveform.

For example, when a metallic particle enters the collection chamber 28, an energized coil, in accordance with well-known theory, introduces eddy currents in the particle. The eddy currents are a function, among other properties, of material conductivity. Thus, when a metallic particle enters the collection chamber 28, eddy currents in the particle cause the effective inductance of the energized coil to decrease. Consequently, the oscillator 44 will produce the oscillating waveform with an increased frequency. Because eddy currents are a function of material conductivity, the greater the size of a particle or the greater amount of particle accumulation, the greater the change in the oscillating waveform frequency.

Advantageously, the present invention is particularly suited to detect the presence of both ferrous and non-ferrous metallic particles. As is well known, eddy current principles apply to both ferrous and non-ferrous metallic particles. Further, because the coils are being energized at such high frequencies, the eddy current inductive effects are dominant over any ferromagnetic inductive effects that are caused by an increase in permeability of the energized coil's magnetic circuit due to the accumulation of ferrous magnetic particles. Consequently, the change in frequency of the oscillating waveform is due to the eddy current inductive effects on both the ferrous and non-ferrous particles.

The oscillating waveform is delivered to a counter 48, which tallies the number of pulses associated with the oscillating waveform and responsively produces first and second control signals. The control signals are pulse-width-modulated and are used to control the energization of the coils 34, 36, 58, as well as, provide information relating to the period of the oscillating waveform. For example, the control signals govern the energization of the coils 34, 36, 58 similar to that shown in the timing diagram of FIG. 5. A multiplexer 46 selects or enables one of the coils 34, 36, 58 based on a predetermined sequence of the control signals. A microprocessor 50 receives the control signals, determines the amount of particle accumulation in the collection chamber 28, and produces a detecting signal having a pulse width modulated waveform.

As shown in FIG. 4, the microprocessor delivers the detecting signal to an electronic monitoring system 52. The electronic monitoring system 52 provides a warning signal to the vehicle operator in response to the duty cycle of the detecting signal being above a predetermined value. The electronic monitoring system 52 may include an LED 54 to provide a visual warning signal and/or a horn 56 to provide an audio warning signal. For example, a warning sinai may be provided in response to the detecting signal having a duty cycle greater than a predetermined value. Further, the microprocessor 50 is able to determine the rate of particle accumulation (trending). The trending data may be accessed by a service tool of a type well-known in the art for downloading diagnostic and prognostic information. Similarly, the trending data may be sent to a remote location via a RF communication link known in the art.

The operation of the electronic circuitry 40 is now described with more particularity. In accordance with the state of the first and second control signals, the multiplexer selects the reference coil 36 to begin energization, while the counter 48 tallies the number of pulses associated with the oscillating waveform. Once the number of pulses reaches a predetermined number, the counter changes the state of the control signals to cause the multiplexer 46 to select the first coil 34 to begin energization. Meanwhile, the microprocessor 50 determines the duty cycle of the first control signal. As shown in FIG. 5, the "high" pulse level of the first control signal is responsive to first coil 34 being energized, while the "low" pulse level of the first control signal is responsive to the reference coil 36 being energized. Thus, the duration of the "high" pulse level is responsive to the amount of ferrous and non-ferrous particle accumulation in the collection chamber 28, while the duration of the "low" pulse level is responsive to only fluid temperature.

At predetermined time periods, the microprocessor 50 energizes the electromagnet 60 via driver circuit 62. The energized electromagnet 60 attracts any ferrous particles that are contained in the collection chamber 28 to the area adjacent the electromagnet 60 and second coil 58. Accordingly, the control signals cause the multiplexer 46 to energize the reference coil 36, then after a predetermined number of pulses, the second coil 58 is energized. As shown if FIG. 5, the duration of the "high" pulse level (of the first control signal) is responsive to the second coil 58 being energized, i.e., the amount of ferrous particle accumulation, while the duration of the "low" pulse level (of the first control signal) is responsive to the reference coil 36 being energized, i.e., only the fluid temperature.

While the electromagnet 60 remains energized, the control signals cause the reference coil 36 to energize, then the first coil 58 to energize. Thus, the duration of the "high" pulse level of the first control signal is responsive to the amount of non-ferrous particle accumulation, while the duration of the "low" pulse level is responsive only to the fluid temperature.

Thus, as described, the three-coil debris sensor 32 measures the total amount of particle accumulation, as well as, the total amount of ferrous and non-ferrous particle accumulation. Consequently, the three-coil debris sensor 32 inherently provides for diagnostic capabilities. For example, a ferrous only measurement and a non-ferrous measurement can be summed and compared to a combined ferrous and non-ferrous measurement to determine if the sensor 32 is operating correctly. Moreover, the second coil 58 is energized while the electromagnet is 60 is de-energized to determine if some debris is stuck in the collection chamber 28 or if a "long" piece of debris, e.g., a wire shaving, has entered the collection chamber 28.

Thus, while the present invention has been particularly shown and described with reference to the preferred embodiment above, it will be understood by those skilled in the art that various additional embodiments may be contemplated without departing from the spirit and scope of the present invention.

Industrial Applicability

In operation, the present invention is used to filter out debris from hydraulic fluid or any other type of lubricating fluid and detect the accumulation of both ferrous and non-ferrous particles. As components such as hydraulic pumps and motors wear, tiny particles of ferrous and non-ferrous particles become suspended in the fluid. If one of the components in the hydraulic system becomes excessively worn out and/or is about to fail, the amount of particles suspended in the oil increases substantially. Likewise, the amount of particles in the debris collection chamber will increase substantially.

The electrical signals provided by the debris sensor causes an indicator light to illuminate in the operator compartment indicating impending failure. Further, the debris sensor determines the extent and type of debris in the fluid, which may be used in diagnosing or predicting a failure. For example, trending data is stored in the microprocessor for later download to a service tool.

Other aspects, objects and advantages of the present invention can be obtained from a study of the drawings, the disclosure and the appended claims.

We claim:

1. An apparatus for detecting particles within a fluid, comprising:

a bobbin defining a debris collection chamber;

spaced apart first and second coils wound in a helix about the bobbin, said first coil wound about the debris collection chamber, wherein the induction of the first and second coils are responsive to the particle accumulation within the collection chamber;

an electromagnet wound about the second coil to attract ferrous particles into the proximity of the second coil;

a reference coil wound in a helix about the bobbin and spaced from the first and second coils, said reference coil being wound below the collection chamber, said second coil disposed between said first coil and said reference coil; and an oscillator selectively coupled to the first, second and reference coils for producing an oscillating waveform, wherein the induction of the reference coil is responsive to the fluid temperature, wherein the frequency of the oscillating waveform is a function of the induction of one of the first, second, and reference coils.

2. An apparatus, as set forth in claim 1, including a multiplexer adapted to select one coil to energize at a given time.

3. An apparatus, as set forth in claim 2, wherein the oscillator produces an oscillating waveform having a series of pulses the frequency of which is a function of the one energized coil inductance.

4. An apparatus, as set forth in claim 3, including a counter adapted to tally the number of waveform pulses of the oscillating waveform of the one energized coil, and responsively producing first and second control signals, the counter changing the state of the control signals in response to tallying a predetermined number of pulses, wherein the multiplexer selects the reference coil to energize in response to the state change of the control signals, and wherein the counter tallies the number of waveform pulses of the oscillating associated with the reference coil.

5. An apparatus, as set forth in claim 4, wherein the control signals are continuous pulse width modulated waveforms, and wherein the duration of the first control signal "high" pulse is responsive to the oscillating waveform frequency associated with the one coil and the duration of the first control signal "low" pulse is responsive to the oscillating waveform frequency associated with the reference coil.

6. An apparatus, as set forth in claim 5, including a microprocessor adapted to receive the control signals, determine the particle accumulation in the collection chamber, and produce a detecting signal having a pulse width modulated waveform indicative of the particle accumulation in the collection chamber.

7. An apparatus, as set forth in claim 6, including an electronic monitoring system adapted to receive the detecting signal and produce a warning signal in response to the detecting signal duty cycle being greater than a predetermined value.

8. An apparatus, as set forth in claim 1, including:

an inlet port;

a screen being substantially cylindrical in shape and having a pair of open ends, the inlet port and screen being disposed such that fluid entering the inlet port flows into the screen chamber through one of the open ends;

a screen chamber being substantially cylindrical in shape and of larger diameter than the screen, the screen being disposed within the screen chamber, the screen chamber being connected to the debris collection chamber; and an outlet port connected to the screen chamber.

9. An apparatus, as set forth in claim 8, including a bypass means for directing fluid flow between the inlet port and the screen chamber without flowing through one of the open ends.

10. An apparatus, as set forth in claim 8, wherein the inlet port and the screen chamber are disposed substantially at a right angle.

11. An apparatus, as set forth in claim 9, wherein the outlet port and screen chamber are disposed substantially at a right angle.

12. An apparatus, as set forth in claim 9, wherein fluid flows substantially radially outwardly through the screen and the bypass means directs fluid flow from the inlet port downwardly and radially inwardly into the screen chamber.

13. An apparatus, as set forth in claim 9, wherein fluid flows substantially radially outwardly through the screen and the bypass means directs fluid flow from the inlet port radially inwardly into the screen chamber and toward the debris collection chamber.

14. An apparatus, as set forth in claim 8, wherein the debris collection chamber is located below the screen chamber and is in fluid communication with the screen chamber whereby debris filtered out of the fluid is pulled toward the debris collection chamber by gravity.

15. An apparatus, as set forth in claim 9, wherein fluid flow from the bypass means dislodges particles from the screen and urges debris toward the debris collection chamber.

16. A method of operating an apparatus for detecting particles within a fluid, the apparatus comprising:

a bobbin defining a debris collection chamber;

spaced apart first and second coils wound in a helix about the bobbin, said first coil wound about the debris collection chamber, wherein the induction of the coils are responsive to the particle accumulation within the collection chamber;

a reference coil wound in a helix about the bobbin, said reference coil being wound below the collection chamber, said second coil disposed between said first coil and said reference coil;

an electromagnet wound about the second coil; and an oscillator selectively coupled to the first, second and reference coils for producing an oscillating waveform, wherein the induction of the reference coil is responsive to the fluid temperature, wherein the frequency of the oscillating waveform is a function of the induction of one of the first, second, and reference coils;

the method comprising the steps of:

energizing the first coil and determining the resulting frequency of the oscillating waveform; thereafter energizing the reference coil and determining the resulting frequency of the oscillating waveform; and responsively determining the amount of particle accumulation of the ferrous and non-ferrous particles in the collection chamber.

17. A method, as set forth in claim 16, including the steps of:

energizing the electromagnet to attract ferrous particles into the proximity of collection chamber adjacent the second coil;

energizing the first coil and determining the resulting frequency of the oscillating waveform; thereafter energizing the reference coil and determining the resulting frequency of the oscillating waveform; and responsively determining the amount of particle accumulation of the non-ferrous particles in the collection chamber.

18. A method, as set forth in claim 17, including the steps of:

energizing the electromagnet to attract ferrous particles into the proximity of collection chamber adjacent the second coil;

energizing the second coil and determining the resulting frequency of the oscillating waveform; thereafter energizing the reference coil and determining the resulting frequency of the oscillating waveform; and responsively determining the amount of particle accumulation of the ferrous particles in the collection chamber.

19. A method, as set forth in claim 18, including the steps of comparing the sum total of the separately determined ferrous and non-ferrous determinations with the combined ferrous and non-ferrous determination in order to determine if the particle detecting apparatus is operating properly.

* * * * *